United States Patent
Lehtonen et al.

(10) Patent No.: US 7,556,728 B2
(45) Date of Patent: Jul. 7, 2009

(54) PROCESS FOR THE MANUFACTURE OF A GASOLINE BLENDING COMPONENT

(75) Inventors: Juha Lehtonen, Porvoo (FI); Jaana Makkonen, Söderkulla (FI)

(73) Assignee: Nestel Oil Oyj, Espoo (FI)

( * ) Notice: Subject to any disclaimer, the term of this patent is extended or adjusted under 35 U.S.C. 154(b) by 223 days.

(21) Appl. No.: 10/681,251

(22) Filed: Oct. 9, 2003

(65) Prior Publication Data
US 2005/0080304 A1    Apr. 14, 2005

(51) Int. Cl.
*C10G 45/04*    (2006.01)
*C07C 5/02*    (2006.01)

(52) U.S. Cl. .................. 208/210; 208/211; 208/144; 208/57; 585/329

(58) Field of Classification Search .............. 208/210, 208/211, 143, 144, 57; 585/329
See application file for complete search history.

(56) References Cited

U.S. PATENT DOCUMENTS

| | | | |
|---|---|---|---|
| 2,135,823 A * | 11/1938 | Lyman et al. ............... | 585/255 |
| 5,177,282 A | 1/1993 | Nierlich et al. | |
| 5,789,643 A | 8/1998 | Herwig et al. | |
| 5,847,252 A * | 12/1998 | Stine et al. ................ | 585/330 |
| 6,329,561 B1 | 12/2001 | Webber et al. | |
| 6,538,168 B1 | 3/2003 | Schwab et al. | |
| 6,548,721 B1 | 4/2003 | Mc Culloch et al. | |
| 6,613,108 B1 | 9/2003 | Aittamaa et al. | |

FOREIGN PATENT DOCUMENTS

| | | |
|---|---|---|
| CN | 1335361 | 2/2002 |
| EP | 0994088 A1 | 4/2000 |
| EP | 1 184 361 A1 | 3/2002 |
| FI | 106955 B | 5/2001 |
| FR | 947166 | 6/1949 |
| GB | 1044771 | 10/1966 |

* cited by examiner

*Primary Examiner*—Tam M Nguyen
(74) *Attorney, Agent, or Firm*—Birch, Stewart, Kolasch & Birch, LLP

(57) ABSTRACT

The present invention relates to a process for the manufacture of paraffinic hydrocarbons, which can be used as gasoline blending components. The obtained gasoline blending component is substantially free of sulphur compounds. The process comprises simultaneous hydrogenation of olefins and degradation of sulphur compounds by hydrogenolysis. In the process a feed-stock containing as impurities sulphur compounds is hydrogenated in two steps in the presence of a noble metal catalyst on aluminium oxide support, and in the first step the major part of olefins are converted and in the secondary step the remaining olefins and sulphur compounds react.

9 Claims, 2 Drawing Sheets

PROCESS FOR THE MANUFACTURE OF A GASOLINE BLENDING COMPONENT

Figure 1:
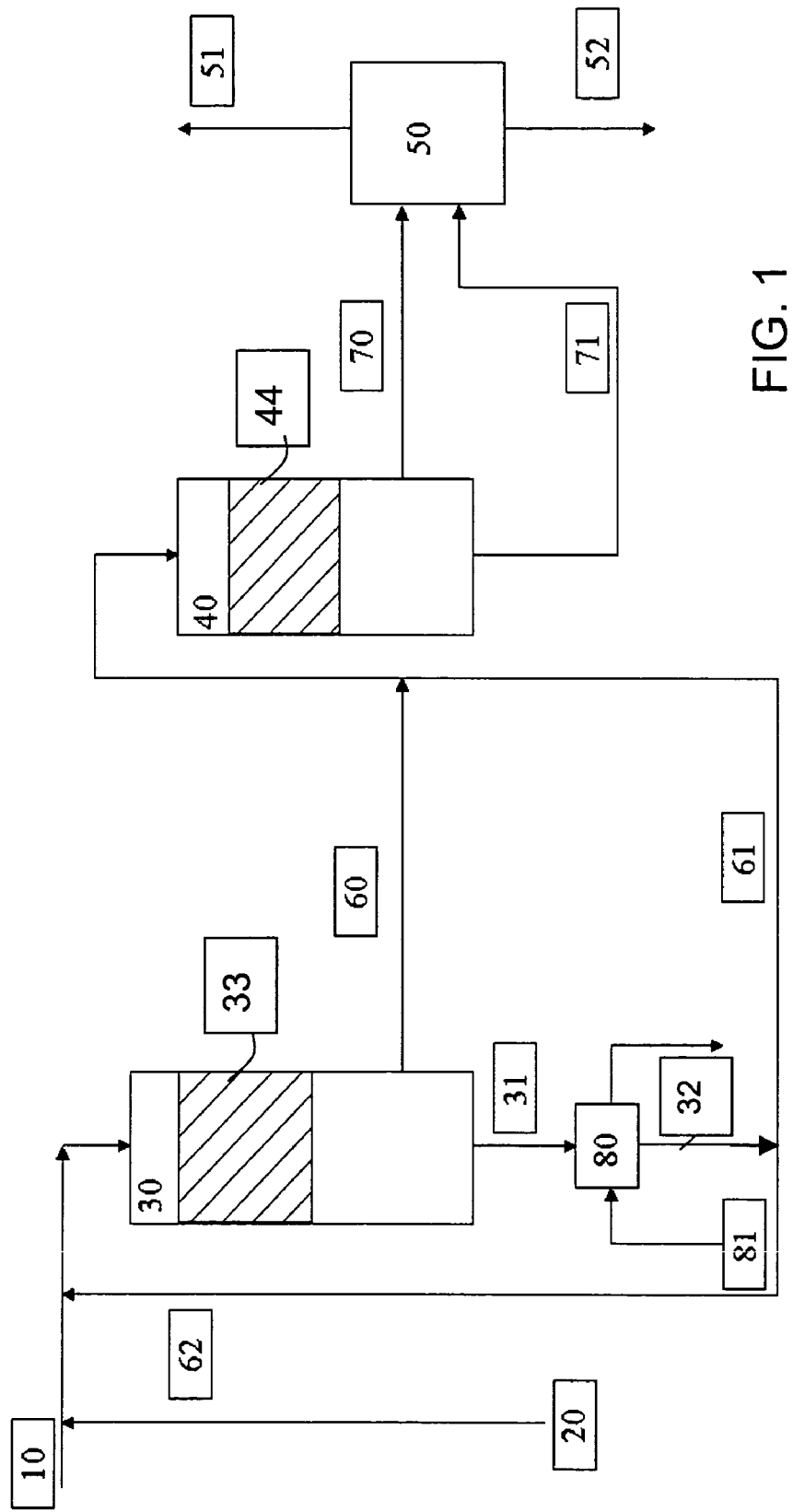

This nonprovisional application claims priority under 35 U.S.C. § 120 on patent application Ser. No. 10/267,957 filed in the UNITED STATES on Oct. 10, 2002, now abandoned which is herein incorporated by reference.

FIELD OF INVENTION

The present invention relates to a process for the manufacture of paraffinic hydrocarbons, which can be used as gasoline blending components. The obtained gasoline blending component is substantially free of sulphur compounds. The process comprises simultaneous hydrogenation of olefins and degradation of sulphur compounds by hydrogenolysis.

STATE OF THE ART

Several methods are known in the prior art for the production of isooctane and for dimerization of isobutene. A process for the manufacture of isooctane from a hydrocarbon feed-stock containing isobutene is disclosed in FI 106955 and U.S. Pat. No. 6,613,108. According to said method the hydrocarbon feed-stock is brought into contact with an acidic catalyst, preferably a cationic ion-exchange resin, in the presence of an oxygenated compound at such conditions wherein at least part of the isobutene is dimerized into diisobutene which is then separated and hydrogenated to isooctane.

GB 1044771 discloses a method for removing sulphur compounds from a hydrocarbon feed-stock by hydrogenating sulphur containing compounds present in the feed-stock with a hydrogenating gas over a hydrodesulphurization on catalyst such as a molybdenum catalyst supported on alumina, which hydrocarbon feed-stock and/or hydrogenating gas contains olefins and/or carbon oxides. This method comprises passing a mixture of hydrocarbons in vapour form with the hydrogenating gas over the hydrodesulphurization catalyst to convert the sulphur present into hydrogen sulphide and removing the hydrogen sulphide.

Typically the product obtained from a butene dimerization unit contains as impurities minor amounts of sulphur containing compounds. These impurities affect the utility of the product isooctane as a gasoline blending component. None of the prior art publications teach a simple process for simultaneous hydrogenation of olefins and removal of sulphur containing compounds and it can be seen that there exists an evident need for such a process. In addition none of the prior art publications teach simultaneous hydrogenation of olefins and removal of sulphur containing compound using low excess of hydrogen/olefin feed ratio.

SUMMARY OF THE INVENTION

An object of the present invention is to provide a process for the manufacture of a gasoline blending component containing sulphur-free paraffinic hydrocarbons from a feed mixture comprising olefinic hydrocarbons obtained from dimerization of butenes.

The process according to the invention comprises simultaneous hydrogenation of olefins and degradation of sulphur compounds by hydrogenolysis. The process according to the invention requires low excess of hydrogen.

Characteristic features of the process according to the invention for the manufacture of a gasoline blending component containing sulphur-free paraffinic hydrocarbons are disclosed in the claims.

DETAILED DESCRIPTION OF THE INVENTION

Surprisingly it has been found that the objectives identified above can be met and the disadvantages of the processes according to the prior art can be avoided or substantially decreased by the process of the invention at the given operating conditions. In accordance with the present invention, a hydrocarbon feed-stock containing 80-97 wt % of $C_8$ olefins, 3-20 wt % of $C_{12}$ olefins, 0.1-7 wt % of $C_9$, $C_{10}$, $C_{11}$ and heavier>$C_{12}$ olefins, and optionally minor amounts of lighter $C_6$-$C_7$ olefins, is used. The feed-stock may originate from an olefinic hydrocarbon mixture obtained from dimerization of butenes.

The feed-stock contains as sulphur compounds 1-1000 wt-ppm, typically 1-50 wt-ppm, calculated as sulphur, of sulphides, disulphides, tiophene and/or alkyltiophenes.

Suitable hydrogenation catalysts to be used in the process according to the invention are noble metal catalysts on aluminium oxide support. Preferable noble metals are platinum and/or palladium, particularly preferably platinum. The content of the noble metal on the support is <1 wt %. In some cases the noble metal may be replaced with nickel. The isomerization of high octane trimethyl pentenes and other branched olefins in the feed-stock to less valuable, less branched isomers is suppressed when aluminium oxide is used as the support for the catalyst.

In the process the feed-stock is hydrogenated in two steps. In the first step the major part of $C_8$ olefins is converted but the conversion of heavier olefins and sulphur compounds is rather low. In the second step the remaining $C_8$ olefins, $C_{12}$ olefins and other heavier olefins and sulphur compounds react. The sulphur compounds are converted to light hydrocarbons and hydrogen sulphide.

In the first step the product stream is optionally circulated in order to dilute the concentrated olefin feed and thus the reaction heat is removed safely from the saturation of double bonds.

The reaction temperature in the first step is in the range of 150-230° C. and the pressure is in the range of 20-70 bar.

In the second step a higher reaction temperature is applied in the reactor than in the first step. The reaction temperature is in the range of 180-300° C., typically in the range of 190-260° C., and the pressure is in the range of 20-70 bar.

In the first step the $C_8$ hydrocarbons are hydrogenated with a conversion of more than 70%. The deactivation of the catalysts in the first step can be avoided or at least decreased by using the relatively low reaction temperature disclosed above.

In the first step a fixed-bed three-phase hydrogenation reactor and preferably a trickle-bed or pulse flow reactor is used. The reactor typically performs as a trickle-bed reactor with a more than two times fluid circulation stream when compared with fluid feed. This controls the rise of temperature in the reactor catalyst bed. In a trickle-bed reactor the catalyst is placed in a fixed bed and liquid olefin feed as well as gaseous hydrogen feed flow concurrently downwards through the bed. The preferable flow regimes for this three-phase flow are trickling and pulse flow regimes. Also other flow patterns of three-phase hydrogenation like counter current flow and concurrent up-flow are possible.

High hydrogen concentration in the first step is maintained with fluid circulation and by introducing fresh hydrogen to the first step. Recycled fluid is saturated with dissolved hydrogen. The advantage of high hydrogen concentration in the first step is that it favours olefin hydrogenation and breaking of the sulphur components and at the same time effectively reduces coke formation on the catalyst.

According to the invention, in the process in the first step one reactor or several reactors parallel with each other can be used, or the reactor can be divided into more than one reactor beds with a cooler between each reactor bed. By using interspace coolers the amount of circulation stream can be decreased. The reaction heat can be removed from the process from the circulating stream by process exchangers whereby the reaction heat can be used for preheating of incoming feed-stock to the dimerization unit of butenes, or as an energy source for distillation columns of bottom boilers of dimerization unit of butenes, either directly or indirectly via utility system of the plant or site area. The heat can also be directly used to other process units at site.

The second step is performed in another reactor wherein the remaining part of the $C_8$ olefins and heavier olefins are converted to paraffinic hydrocarbons, and simultaneously the remaining sulphur compounds are degraded by hydrogenolysis reaction. In the second step the reaction product is not circulated in order to keep the feed as concentrated as possible. In the second step the reactor is also typically operated as a trickle-bed reactor, but other flow patterns of fixed-bed three-phase hydrogenation can be applied. The reaction vessel in the second step can optionally be combined to the same reaction vessel of the first reaction step.

Light hydrocarbons, hydrogen sulphide and sulphur containing impurities are separated from the mainly paraffinic $C_8$-$C_{12}$ hydrocarbons containing product in a stabilization column after the reactors.

Figure 2:
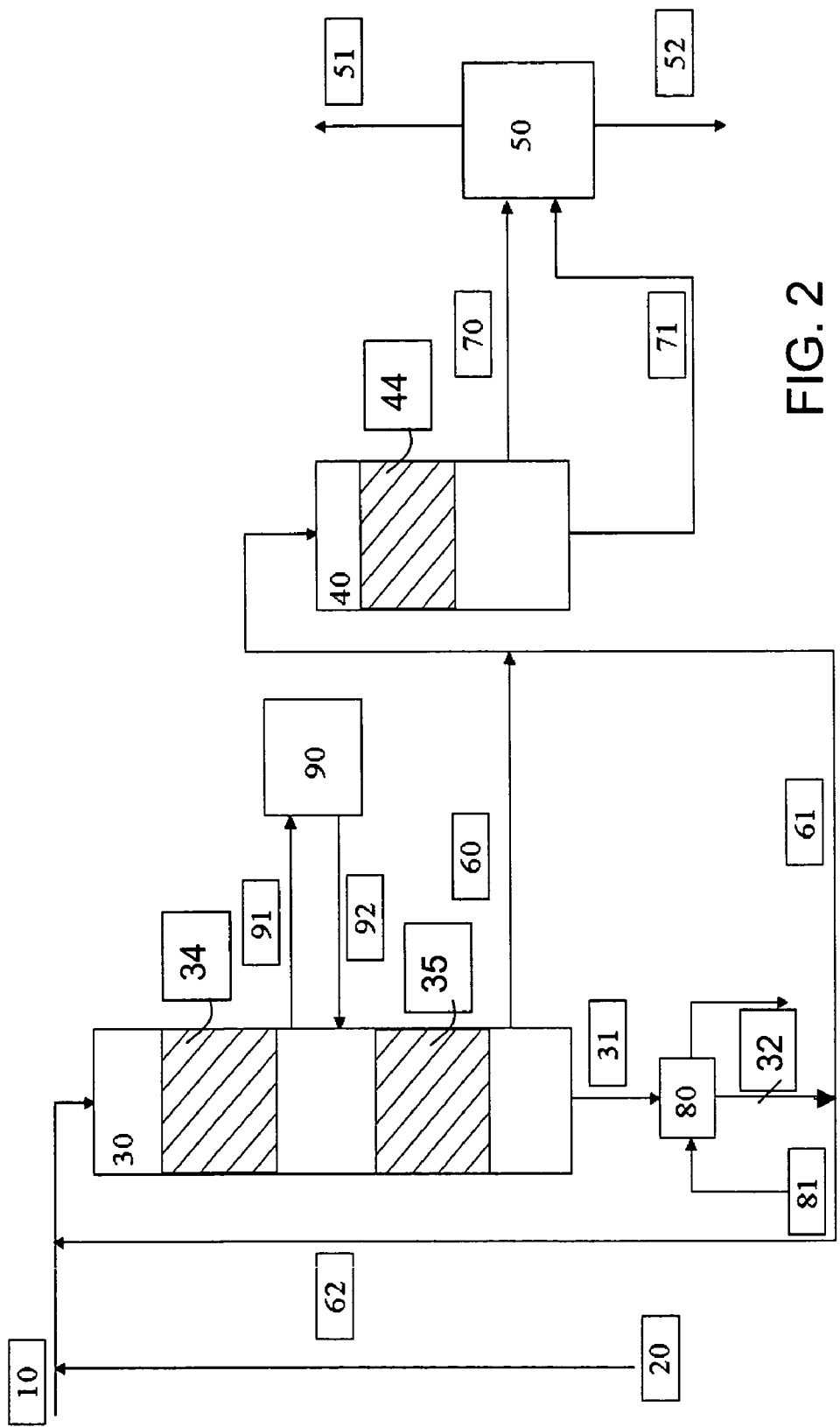

The invention is illustrated in more detail in the FIGS. 1 and 2. These figures merely illustrate some preferable embodiments of the invention to which the scope of the invention is not limited.

LIST OF FIGURES

FIG. 1 describes schematically a preferable embodiment of the process according to the invention FIG. 2 describes schematically another preferable embodiment of the process according to the invention In FIG. 1 in the first step, hydrocarbon feed 10 and fresh hydrogen feed 20 are combined before entering the primary reactor 30. The combined feed, 10 and 20, is passed through the catalyst bed 33 in the primary reactor 30 and the gas flow 60 and the liquid flow 31 are separated from each other in the lower part of the reactor. The liquid flow 31 is cooled in the heat exchanger 80 using for cooling an out-coming process flow 81 from dimerization of butene. After cooling the liquid flow 32 is divided into recycling flow 62 which is returned to the combined feed 10 and 20, and into flow 61, which is passed to the second step, into the secondary reactor 40. The flow 61 is combined with the gas flow 60 containing the gaseous products from the first step before entering the secondary reactor 40 in the second step. The combined flow 60 and 61, is then passed to the catalyst bed 44 in the reactor 40 and the gas flow 70 and the liquid flow 71 are separated from each other in the lower part of the reactor 40 and they are passed to a stabilization column 50 wherein hydrogen and other light components are separated as flow 51 from the paraffinic product flow 52.

In FIG. 2 another embodiment of the present invention is disclosed wherein the primary reactor in the first step is divided into two catalyst beds with an outlet for a liquid product flow between the catalyst beds. After the first catalyst bed the liquid product flow is cooled and returned to the second catalyst bed. Optionally the cooling may be built in the reactor.

In FIG. 2 in the first step the hydrocarbon feed 10 and the fresh hydrogen feed 20 are combined before the primary reactor 30. The combined feed 10 and 20 is passed through the first catalyst bed 34 in the reactor 30. After the catalyst bed 34 the gas flow and the liquid flow are separated and the liquid flow 91 is passed to the heat exchanger 90 for cooling. The cooled liquid flow 92 is returned to the second catalyst bed 35 and then the gas flow 60 and the liquid flow 31 are separated from each other in the lower part of the reactor. The heat exchanger 90 may operate like the heat exchanger 80 using as cooling fluid the process flow from dimerization of butene. The liquid flow 31 is cooled in the heat exchanger 80 with an out-coming process flow 81 from dimerization of butene. Then after cooling, the liquid flow 32 is divided into recycling flow 62 and into flow 61, which is passed to the second step into the secondary reactor 40. The flow 61 is combined with the gas flow 60 containing the gaseous products from the first step, before entering the secondary reactor 40 in the second step. The combined flow 60 and 61, is then passed to the catalyst bed 44 in the reactor 40 and the gas flow 70 and the liquid flow 71 are separated from each other in the lower part of the reactor 40 and they are passed to a stabilization column 50 wherein hydrogen and other light components are separated as flow 51 from the paraffinic product flow 52.

The process according to the invention for the manufacture of a gasoline blending component has several advantages when compared to the state of the art. The removal of sulphur compounds and olefin saturation takes place inside the same reactor at mild operation conditions. The same catalyst containing less than 1 wt % of noble metal on aluminium oxide support is used for the hydrogenation of both $C_8$ and heavier $C_{12}$ olefins. The use of aluminium oxide support for the noble metal catalyst prevents the isomerization of branched high octane gasoline components to less branched low octane components, which happens considerably when aluminium oxide/silica support is used. The lower reaction temperature in the reactor(s) in the first step decreases the deactivation of the catalyst. Further, the circulation of the product stream in the reactor(s) in the first step, as well as the circulation of any intermediate stream originating from any of the hydrogenation reactors, ensures the safe control of the temperature. In the second step there is no circulation and the concentrated feed enables the conversion of the remaining unreacted material.

A further advantage of the invention is the possibility to use hydrogen/olefin ratio close to required stoichiometric consumption, in order to achieve the required olefin conversion and removal of sulphur. The hydrogen/olefin molar ratio is from 0.9 to 2.0, preferably from 1.05 to 1.5, resulting in low hydrogen consumption. Low excess of hydrogen and mild operating conditions decrease hydrogen loss with vapour product and a hydrogen recycling compressor is not normally needed for hydrogen recovery.

The invention is further illustrated with the following examples, which however are not considered as limiting the scope of the invention.

EXAMPLES

Example 1

Hydrogenation of Olefins and Degradation of Sulphur Compounds in a Two-Step Process, and Quality of the Product Obtained, as Gasoline Blending Component $C_8$-$C_{12}$ olefin feed containing 13 wt-ppm of sulphur compounds, calculated as sulphur, in the feed-stock, was hydrogenated in a two-step process using a platinum catalyst with 0.3 wt % of platinum on aluminium oxide support. The hydrogenation was performed in two steps, where a circulation flow 6 times the fresh feed flow was applied in the first step, and the second step was operated without any circulation flow. In the first step the temperature was around 180° C. and in the second step 220° C.

In first step the conversion of octenes was 92% and the selectivity of 2,4,4-trimethylpentenes to isooctane was 98%. The feed contained 5 wt % of dodecenes. 30 wt % of 2,2,6,6-tetra-4-methylene-heptane was converted, 2,2,4,6,6-pentamethyl-3-heptene (trans) and 2,2,4,6,6-pentamethyl-3-heptene (cis) were not converted at all.

In the second step at 220° C. the conversion of octenes was around 100% and of dodecenes respectively 83-94%. The total olefin conversion was then 94% and the selectivity of 2,4,4-trimethylpentenes to isooctane was 100%. The sulphur content was reduced from 13 wt-ppm in the feed-stock to 0.6 wt-ppm in the product. The components of the final product were analyzed using a gas chromatographic method. The results of (PONA=paraffines, olefins, naphthenes, aromatics) analysis are presented in the following table 1 and other test results in table 2:

TABLE 1

PONA analysis

| Carbon number | Paraffines | Olefines | Naftenes | Aromatics | Dienes | Others | Total |
|---|---|---|---|---|---|---|---|
| 3 | 0.001 | | | | | | 0.001 |
| 4 | 0.759 | | | | | 0.117 | 0.876 |
| 5 | 0.007 | | | | | | 0.007 |
| 6 | 0.018 | | | | | | 0.018 |
| 7 | 0.016 | | 0.006 | 0.01 | | 0.017 | 0.049 |
| 8 | 86.992 | 0.083 | 0.139 | | | 0.249 | 87.463 |
| 9 | | | | | | 0.035 | 0.035 |
| 10 | 0.012 | | 0.004 | | | | 0.016 |
| 11 | 0.006 | | 0.029 | | 0.003 | 0.009 | 0.047 |
| 12 | 7.745 | 1.774 | | | 0.113 | | 9.632 |
| 13 | 0.027 | 0.063 | | | | | 0.090 |
| 14 | | | | | | | 0.000 |
| 15 | 0.013 | 0.012 | | | | | 0.025 |
| 16 | 1.468 | 0.152 | | | 0.012 | | 1.632 |
| 17 | | | | | | | 0.000 |
| 18 | 0.075 | 0.024 | | | | 0.011 | 0.110 |
| Total | 97.139 | 2.108 | 0.178 | 0.01 | 0.128 | 0.438 | 100.00 |

TABLE 2

Other test results

| Test | Result | Method used |
|---|---|---|
| Sulphur Content | 0.6 wt-ppm | ASTM D-3120 |
| RON (research octane number) | 98.5 | ASTMD-2699-97 (1998) |
| MON (motor octane number) | 96.0 | ASTM D-2700-95a (1998) |
| Oxidation Stability | >1500 min | EN ISO 7536 |
| Existent and Potential Gum | <1 mg/100 ml | EN ISO 6246 |
| RVP (Reid vapour pressure) | 20.9 kPa | EN 13016 |
| Density/15° C. | 708.8 kg/m$^3$ | ISO 12185 |
| Distillation | See table 3. | ISO 3405 |

TABLE 3

| Distillation results | |
|---|---|
| Start | 72.1° C. |
| 5 vol-% | 97.0° C. |
| 10 vol-% | 99.9° C. |
| 20 vol-% | 101.8° C. |
| 30 vol-% | 102.6° C. |
| 40 vol-% | 102.6° C. |
| 50 vol-% | 104.2° C. |
| 60 vol-% | 104.9° C. |
| 70 vol-% | 106.6° C. |
| 80 vol-% | 110.8° C. |
| 90 vol-% | 127.3° C. |
| 95 vol-% | 171.0° C. |
| End | 205.6° C. |
| Yield | 98.2 vol-% |
| Residual | 1.2 vol-% |
| Loss | 0.6 vol-% |
| E-70 | 0.0 vol-% |
| E-100 | 9.7 vol-% |
| E-150 | 92.1 vol-% |
| E-180 | 96.2 vol-% |

Example 2

The Effect of Support Selection on the Isomerization of 2,4,4-Trimethylpentenes

| | |
|---|---|
| Catalyst 1: | palladium <1 wt %, on $Al_2O_3$ support |
| Catalyst 2: | palladium <1 wt %, on $Al_2O_3/SiO_2$ support |
| Feed: | 2,4,4-trimethylpentenes |
| Conditions: | Temperature: 150° C. |
| | Pressure: 30 bar |
| | WHSV: 1 l/h |
| Reactor system: | laboratory scale tube reactor |

The conversion and selectivity are presented in the following table 4.

TABLE 4

Conversion and selectivity of isomerization of 2,4,4-trimethylpentenes

| Catalyst | Conversion of 2,4,4-trimethylpentenes | Selectivity to isooctane |
|---|---|---|
| Catalyst 1 | 99.9 | 99.8 |
| Catalyst 2 | 98.9 | 58.5 |

Example 3

Hydrogenation of Olefin Feed and Degradation of Sulphur Compounds in a Two-Step Process Using Low Excess of Hydrogen $C_8$-$C_{12}$ olefin feed-stock from dimerisation of butenes was hydrogenated in a two-step facility using a platinum catalyst with 0.3 wt-% of platinum on aluminium oxide support in the reactors. A circulation flow 6.5 times the fresh feed flow was applied in the first step, and the second step was operated without any circulation flow. In the first step an average operating temperature in the reactor was 190-198° C. and in the second step an average operating temperature was 210-218° C. Operating pressure in the first step was 29 bar and in the second step 28 bar.

The feed-stock contained 0.94% of $C_4$-$C_{16}$ paraffins, 94.0% of $C_8$ olefins, 4.30% of $C_{12}$ olefins, aromatics 0.43% and 0.4% others. The feed contained 3 wt-ppm sulphur compounds, calculated as sulphur. Hydrogen was introduced only to the first step. Hydrogen effluent from the first stage was introduced to the second stage. The hydrogen/olefin molar ratio in the feed was 1.07. The product stream was stabilised by distillation and analysed by a gas chromatographic method.

The product had the following composition: 96.9% total paraffins, 0% $C_8$ olefins, 2.49% $C_{12}$ olefins, 0.46% aromatics and 0.15 others. $C_8$ olefins conversion was 100%. Sulphur content was below the detection limit (<0.1 wppm).

The invention claimed is:

1. A process for the manufacture of a gasoline blending component containing paraffinic hydrocarbons and being essentially free of sulphur compounds, comprising hydrogenating in two steps a mainly olefinic liquid feed-stock comprising olefins, and sulphur compounds as impurities, in the presence of hydrogen and a noble metal catalyst on aluminium oxide support, wherein in the first step the major part of olefins are converted and in the secondary step the remaining olefins and sulphur compounds react, wherein a trickle-bed reactor is used in the first step and in the second step, wherein the feed-stock comprises 80-97 wt % of $C_8$ olefins, 3-20 wt % of $C_{12}$ olefins, and 0.1-7 wt % of $C_9$, $C_{10}$, $C_{11}$ and olefins heavier than $C_{12}$, wherein the reaction temperature in the first step is in the range of 150-230° C. and the pressure is in the range of 20-70 bar and in the second step the temperature is in the range of 190-260° C. and the pressure is in the range of 20-70 bar, wherein the reaction temperature in the second step is higher than the reaction temperature in the first step, wherein the hydrogen feed/olefin feed molar ratio is from 0.9 to 2.0, and wherein the concentration of the noble metal in the noble metal catalyst is less than 1 wt %.

2. A process for the manufacture of a gasoline blending component containing paraffinic hydrocarbons according to claim 1, wherein the feed-stock further comprises minor amounts of lighter $C_6$-$C_7$ olefins and 1-1000 wt-ppm of sulphur compounds, calculated as sulphur.

3. A process for the manufacture of a gasoline blending component containing paraffinic hydrocarbons according to claim 1, wherein the feed-stock originates from a mixture obtained from a dixuerization of butenes.

4. A process for the manufacture of a gasoline blending component containing paraffinic hydrocarbons according to claim 1, wherein the feed-stock contains as sulphur compounds mainly sulphides, disulphides, thiophene and/or alkylthiophenes.

5. A process for the manufacture of a gasoline blending component containing paraffinic hydrocarbons according to claim 1, wherein the noble metal catalysts comprises platinum, palladium or a combination thereof.

6. A process for the manufacture of a gasoline blending component containing paraffinic hydrocarbons according to claim 1 wherein the noble metal catalysts comprises platinum.

7. A process for the manufacture of a gasoline blending component containing paraffinic hydrocarbons according to claim 1 wherein the reaction heat is removed from the process and the reaction heat is used for preheating of incoming feed-stock to the a dimerization unit of butenes, or as an energy source for distillation columns of bottom boilers of dimerization unit of butenes.

8. A process for the manufacture of a gasoline blending component containing paraffinic hydrocarbons according to claim 1, wherein in the first step the product stream is circulated in the reactor(s).

9. A process for the manufacture of a gasoline blending component containing paraffinic hydrocarbons according to claim 1, wherein the hydrogen feed/olefin feed molar ratio is 1.0-1.5.

* * * * *